(12) United States Patent
Soppimath et al.

(10) Patent No.: US 9,180,093 B2
(45) Date of Patent: *Nov. 10, 2015

(54) STABLE BORTEZOMIB FORMULATIONS

(75) Inventors: Kumaresh Soppimath, Monmouth, NJ (US); Satish Pejaver, Bridgewater, NJ (US); Kanaiyalal R. Patel, Union, NJ (US); Lakkaraju Dasaradhi, Princeton Junction, NJ (US); Rama Sodum, Princeton, NJ (US); Hari Desu, Plainsboro, NJ (US); Navneet Puri, Bridgewater, NJ (US)

(73) Assignee: Innopharma, Inc., Piscataway, NJ (US)

( * ) Notice: Subject to any disclaimer, the term of this patent is extended or adjusted under 35 U.S.C. 154(b) by 40 days.

This patent is subject to a terminal disclaimer.

(21) Appl. No.: 13/592,235

(22) Filed: Aug. 22, 2012

(65) Prior Publication Data

US 2012/0322763 A1 Dec. 20, 2012

Related U.S. Application Data

(60) Division of application No. 13/431,313, filed on Mar. 27, 2012, now Pat. No. 8,263,578, which is a continuation-in-part of application No. 13/051,102, filed on Mar. 18, 2011.

(60) Provisional application No. 61/315,080, filed on Mar. 18, 2010.

(51) Int. Cl.
| | | |
|---|---|---|
| A61K 31/69 | (2006.01) | |
| A61K 31/4965 | (2006.01) | |
| A61K 9/00 | (2006.01) | |
| A61K 9/08 | (2006.01) | |
| A61K 47/10 | (2006.01) | |
| A61K 9/19 | (2006.01) | |
| C07B 63/04 | (2006.01) | |

(52) U.S. Cl.
CPC .............. *A61K 9/08* (2013.01); *A61K 9/0019* (2013.01); *A61K 31/4965* (2013.01); *A61K 31/69* (2013.01); *A61K 47/10* (2013.01); *C07B 63/04* (2013.01); *A61K 9/19* (2013.01)

(58) Field of Classification Search
CPC ..... A61K 31/69; A61K 47/10; A61K 9/0019; A61K 9/08; A61K 9/19; A61K 31/4965; C07B 63/04

See application file for complete search history.

(56) References Cited

U.S. PATENT DOCUMENTS

| | | | |
|---|---|---|---|
| 4,525,309 A | 6/1985 | Matteson et al. | |
| 5,780,454 A | 7/1998 | Adams et al. | |
| 6,083,903 A | 7/2000 | Adams et al. | |
| 6,297,217 B1 | 10/2001 | Adams et al. | |
| 6,617,317 B1 | 9/2003 | Adams et al. | |
| 6,699,835 B2 | 3/2004 | Plamondon et al. | |
| 6,713,446 B2 | 3/2004 | Gupta | |
| 6,747,150 B2 | 6/2004 | Adams et al. | |
| 6,958,319 B2 | 10/2005 | Gupta | |
| 7,109,323 B2 | 9/2006 | Plamondon et al. | |
| 7,119,080 B2 | 10/2006 | Adams et al. | |
| 8,063,095 B2 | 11/2011 | Laurent et al. | |
| 8,263,578 B2* | 9/2012 | Soppimath et al. .............. 514/64 |
| 2005/0240047 A1 | 10/2005 | Pickersgill et al. | |
| 2006/0084691 A1 | 4/2006 | Piperdi | |
| 2006/0159736 A1 | 7/2006 | Zalipsky et al. | |
| 2007/0116729 A1 | 5/2007 | Palepu | |
| 2007/0197473 A1 | 8/2007 | Frankel et al. | |
| 2008/0038316 A1 | 2/2008 | Wong et al. | |
| 2009/0062222 A1 | 3/2009 | Sherman et al. | |
| 2009/0092661 A1 | 4/2009 | Huang et al. | |
| 2009/0099132 A1 | 4/2009 | Olhava et al. | |
| 2009/0192140 A1 | 7/2009 | Laurent et al. | |
| 2009/0222080 A1 | 9/2009 | Jukema et al. | |
| 2010/0113392 A1 | 5/2010 | Badros | |
| 2010/0135984 A1 | 6/2010 | Hyde et al. | |
| 2010/0137246 A1 | 6/2010 | Hyde et al. | |
| 2010/0226597 A1 | 9/2010 | Palle et al. | |
| 2011/0178470 A1 | 7/2011 | Kocherlakota et al. | |
| 2011/0230441 A1 | 9/2011 | Soppimath et al. | |
| 2012/0035133 A1 | 2/2012 | Bricout et al. | |

FOREIGN PATENT DOCUMENTS

| | | | |
|---|---|---|---|
| CA | 2583520 A1 | 10/2006 | |
| EP | 2238973 A1 | 10/2010 | |
| JP | 2003-508436 A | 3/2003 | |
| JP | 2004-517931 A | 6/2004 | |
| JP | 2004-517932 A | 6/2004 | |
| JP | 2007-513084 A | 5/2007 | |
| KR | 10-2008-0067705 A | 7/2008 | |
| WO | 2006-134864 A1 | 12/2006 | |
| WO | 2008/057456 A2 | 5/2008 | |

(Continued)

OTHER PUBLICATIONS

U.S. Appl. No. 13/592,228, Aug. 2012, Soppimath et al., 514/64.*
Andre, P. et al., "Stability of bortezomib 1-mg/mL solution in plastic syringe and glass vial", Ann Pharmacother, Sep. 2005, 39(9), 1462-1466 (abstract).
Hsieh F.Y. et al., "Elucidation of potential bortezomib response markers in multiple myeloma patients", Journal of Pharmaceutical and Biomedical Analysis, vol. 49, pp. 115-122, 2009.
Pekol, T. et al., "Human Metabolism of the Proteasome Inhibitor Bortezomib: Identification of Circulating Metabolites", The American Society for Pharmacology and Experimental Therapeutics, vol. 33, No. 6, 2005.
Stella, V.J. et al., "Prodrug strategies to overcome poor water solubility", Advanced Drug Delivery Reviews, vol. 59, pp. 677-694, 2007.

(Continued)

*Primary Examiner* — Kara R McMillian
(74) *Attorney, Agent, or Firm* — Fish & Tsang, LLP

(57) ABSTRACT

Multi-dose formulations for bortezomib are presented in which bortezomib has significantly improved stability. Especially preferred formulations include those in which bortezomib is in a liquid form suitable for injection, wherein the solvent system predominantly comprises propylene glycol. In other preferred aspects, bortezomib is present as a Lewis donor-acceptor complex with a hetero-bifunctional Lewis base.

20 Claims, No Drawings

(56) References Cited

FOREIGN PATENT DOCUMENTS

| WO | 2008/075376 | 6/2008 |
|---|---|---|
| WO | 2009/102707 | 8/2009 |
| WO | 2010/039762 | 4/2010 |
| WO | 2010/089768 | 8/2010 |
| WO | 2010/114982 | 10/2010 |

OTHER PUBLICATIONS

Vanderloo, J.P. et al., "Stability of unused reconstituted bortezomib in original manufacturer vials", Journal of Oncological Pharmaceutical Practice, Oct. 6, 2010 (abstract).

Wu, S. et al., "Degradation Pathways of a Peptide Boronc Acid Derivative, 2-Pyz-(C))-Phe-Leu-B(OH)2", Department of Pharmaceutical Chemistry, the University of Kansas, 2000.

Bolognese, A. et al.; An NMR Study of the Bortezomib Degradation under Clinical Use Conditions; Advances in Hematology; vol. 2009, Article ID 704928, 5 pages; Hindawi Publishing Corporation.

Baker, S.J., et al., "Therapeutic Potential of Boron-Containing Compounds," Future Med. Chem. (2009) 1(7), 1275-1288.

ISA/KR, International Search Report and Written Opinion, International Application No. PCT/US2011/029003, Dec. 23, 2011, 9 pages.

EPO, Extended European Search Report (EESR), EPO Application No. 11757060.6, Apr. 2, 2014, 12 pages.

EPO, Extended European Search Report (EESR), EPO Application No. 12183276.0, May 10, 2013, 4 pages.

* cited by examiner

STABLE BORTEZOMIB FORMULATIONS

This application is a divisional application of our non-provisional U.S. application with the Ser. No. 13/431,313 (allowed), which was filed Mar. 27, 2012, which is a continuation-in-part application of our co-pending non-provisional U.S. application with the Ser. No. 13/051,102, which was filed Mar. 18, 2011, and which claims the benefit of priority to U.S. provisional application with the Ser. No. 61/315,080, which was filed Mar. 18, 2010.

FIELD OF THE INVENTION

The field of the invention is bortezomib formulations with improved stability, and particularly storage-stable multi-dose liquid bortezomib formulations.

BACKGROUND

Bortezomib ((N-(2-pyrazine) carbonyl-L-phenylalanine-L-leucine boronic acid); sold as Velcade™, Millennium Pharmaceuticals) is a 26S proteasome inhibitor that is approved for use in treating various neoplastic diseases, and especially treatment of relapsed multiple myeloma and mantle cell lymphoma. It is believed that the boron atom in bortezomib binds to the catalytic site of the proteasome, ultimately leading to proteasome inhibition and reduced degradation of pro-apoptotic factors, which in turn triggers apoptosis in treated cells. Bortezomib and related compounds are described in U.S. Pat. Nos. 5,780,454, 6,083,903, 6,297,217, 6,617,317, 6,713,446, 6,747,150, 6,958,319, 7,119,080. These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

Unfortunately, many aminoalkylboronic acids (including bortezomib) will undergo a spontaneous 1,3-rearrangement to give the homologous amines, owing to the instability of free α-amino groups. These compounds yield boric acids and alcohols by degradation and undergo oxidative reactions that easily destroy the C—B bond which is longer and weaker than the corresponding C—C bond (see e.g., Adele Bolognese, Anna Esposito, MicheleManfra, Lucio Catalano, Fara Petruzziello, Maria CarmenMartorelli, Raffaella Pagliuca, VittoriaMazzarelli, Maria Ottiero, Melania Scalfaro, and Bruno Rotoli. Advances in Hematology, 2009 (2009) 1-5). Such instability is borne out in stress testing and accelerated stability studies of bortezomib that has established that bortezomib in aqueous solution for injection is intrinsically unstable. For example, in an ethanol:normal saline solution (2:98, pH 2.8), Bortezomib (0.5 mg/mL) degraded 20% at 25° C. in 1 month, and in propylene glycol:ethanol:water (50:10:40), the stability of the compound improved, but still degraded 20% in 8 months when stored at 25° C. Among other factors, it was speculated that the degradation of Bortezomib observed in PEG300:EtOH:$H_2O$ (40:10:50) solvent might be due to the presence of peroxides, as PEG300 is known to undergo auto-oxidation with concomitant peroxide generation. (Journal of Pharmaceutical Sciences, 89, 2000 758-765).

In other studies, bortezomib was reported to be susceptible to oxidative degradation under a number of experimental conditions, and that the oxidation of alkyl boranes (which yields the ester of boric acid) can also be due to reaction with alkyl peracids, alkyl peroxides, or oxygen radical species. (Brown H C. 1972. Boranes in organic chemistry. Ithaca, N.Y.: Cornell University Press.) The initial oxidation can be attributed to peroxides or molecular oxygen and its radicals and as light, metal ions, and alkaline conditions normally facilitate oxidation. These conditions are therefore not considered favorable to the stability of bortezomib or any other alkyl boronic acid derivative. (Hussain M A, Knabb R, Aungust B J, Kettner C. 1991. Anticoagulant activity of a peptide boronic acid thrombin inhibitor by various routes of administration in rats. Peptides 12:1153-1154).

Formation of boronic esters from diol and polyols was reported by Kuivila et al. reporting the preparation of several esters of phenylboronic acid by reaction with sugars like mannitol and sorbitol, and 1,2-diols like catechol and pinacal. (J. Org. Chem. 1954, 8, 780-783), and reversible formation of boronic ester by the interaction of boronic acids and polyols in water was first noted by Lorand and Edwards. (J. Org. Chem. 1959, 24, 769-774). U.S. Pat. Nos. 7,119,080, 6,713,446, 6,958,319, 6,747,150, and 6297217 disclose formation of diester of boronic acid functional group with mannitol after lyophilization. From the so formed ester, the active boronic acid is obtained upon reconstitution of the drug product in saline solution for injection. Similarly, attempts to form the ester of boronic acid with alpha-hydroxy and beta-carboxylic acids like citric acid along with bulking agents and buffers was disclosed in WO 2009/154737.

To circumvent issues with stability of bortezomib in solution, the compound can be lyophilized and reconstituted prior to injection. However, while such an approach tends to solve the issues associated with bortezomib stability, unused reconstituted solution must be injected within hours or days (see e.g., Stability of unused reconstituted bortezomib in original manufacturer vials; J Oncol Pharm Pract. 2010 Oct. 6, or Stability of bortezomib 1-mg/mL solution in plastic syringe and glass vial; Ann Pharmacother. 2005 September; 39(9): 1462-6). Similarly, bortezomib esters of mannitol when reconstituted are suitable only for administration within 8 hr when stored at room temperature. Still further known approaches include isolation of specific polymorphic forms having improved stability as described in WO2008075376A1, and lyophilized forms with tromethamine as described in WO2010089768A2. Yet other formulations with selected organic solvents and other ingredients are described in WO2010039762A2. Unfortunately, all or almost all of such known compositions fail to provide significant stability for bortezomib, especially storage stability where the formulation is a liquid formulation.

Therefore, even though there are many formulations for bortezomib known in the art, all or almost all of them suffer from limited stability when bortezomib is in solution, particularly over extended periods. Consequently, currently used products fail to provide flexibility of dosing. More importantly, the currently known or marketed products do not allow for ready-to-use multi-dose liquid formulations having extended stability. Thus, there is still a need to provide improved liquid bortezomib formulations with greater stability.

SUMMARY OF THE INVENTION

The inventive subject matter is drawn to compositions and methods for bortezomib in solution in which bortezomib has significantly increased stability over prolonged periods of time. In most preferred aspects, contemplated formulations are single phase, substantially non-aqueous liquid formulations, and/or formulations in which bortezomib is formulated with a hetero-bifunctional Lewis base donor compound to form a Lewis donor-acceptor complex.

In one preferred aspect of the inventive subject matter, a liquid single phase multi-dosage pharmaceutical composition is formulated and provided in a suitable container for single or multiple use that includes a liquid formulation comprising bortezomib, wherein the liquid formulation is a substantially non-aqueous solvent system suitable for injection, and wherein the solvent system comprises as a main component propylene glycol. As used herein, the term "multi-dosage" and "multi-dose" are used interchangeably herein, and when used in conjunction with a pharmaceutical composition or formulation, refer to a pharmaceutical composition or formulation that has a volume and/or quantity of the active pharmaceutical ingredient suitable for at least two independent and distinct administrations (to the same or a different patient) of the pharmaceutical composition or formulation. Most preferably, the bortezomib in such formulations is present at a pharmaceutically effective concentration and in an amount sufficient for at least two independent dosages, and the solvent system is formulated to maintain degradation of the bortezomib at a level of less than 10 wt % (more typically equal or less than 8 wt %, and most typically 2-6 wt % and even lower) when the liquid formulation is stored over at least three months at ambient conditions (i.e., 25° C., 60% relative humidity).

It is especially preferred that the substantially non-aqueous solvent system comprises at least 50 vol %, more preferably at least 75 vol %, and most preferably 100 vol % propylene glycol. In such formulations, it is still further preferred that the substantially non-aqueous solvent system further comprises a polar solvent in an amount of equal or less than 50 vol %, more preferably equal or less than 25 vol %, and most preferably equal or less than 15 vol %. Among other choices, the polar solvent is most preferably ethanol. Alternatively, the substantially non-aqueous solvent system may include the polar solvent in an amount of equal or less than 15 vol %, and more typically equal or less than 10 vol %. In such case, the polar solvent is preferably water.

In another preferred aspect of the inventive subject matter, a pharmaceutical composition comprises bortezomib and a hetero-bifunctional Lewis base, wherein the bortezomib and the hetero-bifunctional Lewis base together are present in form of a Lewis donor-acceptor complex, and wherein especially preferred hetero-bifunctional Lewis bases have at least two distinct donor groups (most preferably selected from —NH$_2$, —SH, COOH, and —OH). Such contemplated formulations will preferably be lyophilized in solution.

It is generally preferred that in such formulations bortezomib and the hetero-bifunctional Lewis base are present in a ratio of 1:200, more preferably in a ratio of 5:80, and most preferably in a ratio of 20:40. Most typically, preferred hetero-bifunctional Lewis bases include amino acids (e.g., naturally occurring amino acid or an N-acetylated amino acid), peptides (e.g., naturally or synthetic dipeptides or tripeptides), and substituted polyethylene glycols. Particularly preferred substituted polyethylene glycol have a structure according to Formula I

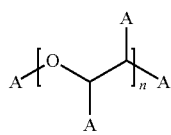

Formula I wherein n is an integer between 2 and 5,000, and wherein each A is independently selected from the group consisting of hydrogen, —NH$_2$, —SH, —COOH, and —OH. Where the composition is lyophilized, it is preferred that the formulation includes a buffering agent, a lyoprotectant, a cryoprotectant, a preservative, and/or an antioxidant.

In yet another aspect of the inventive subject matter, a storage-stable liquid pharmaceutical composition includes bortezomib in a single-phase liquid formulation comprising a substantially non-aqueous solvent system suitable for injection, a buffer, and bortezomib, wherein the bortezomib is present in the formulation at a therapeutically effective concentration (e.g., between 1 mg/ml and 5 mg/ml). In especially preferred compositions, the solvent system comprises as a predominant component (i.e., at least at 50 vol %, more typically at least 70 vol %, most typically at least 90 vol %) propylene glycol. Moreover, it is contemplated that the solvent system, the buffer, and the pH are selected such as to be effective to suppress formation of at least one of an amide degradation product, a first carbinolamide degradation product, and a second carbinolamide degradation product when the liquid formulation is stored under storage conditions (e.g., at least 15 days at 50° C.). Viewed from a different perspective, one particularly preferred non-aqueous solvent system consist essentially of propylene glycol, or comprises at least 70 vol % (and more typically at least 90 vol %) propylene glycol, and includes as especially preferred buffer an aqueous acetate buffer (e.g., at a concentration of between 0.05 and 0.25M), particularly at pH 3.

Thus, the inventors also contemplate a container (e.g., a vial, an ampoule, an intravenous bag, or a syringe) that may or may not be configured as a multi-use container. In such uses, the container includes a quantity of the liquid formulation that is suitable for independent and multiple administrations.

Viewed from another perspective, the inventors also contemplate a method of suppressing formation of a plurality of degradation products of bortezomib in solution. Especially preferred methods include a step of compounding a single-phase liquid formulation from a substantially non-aqueous solvent system suitable for injection, a buffer, and bortezomib, wherein the bortezomib is present in the formulation at a pharmaceutically effective concentration (preferably between 1 mg/ml and 5 mg/ml). Most preferably, the solvent system essentially consists of or comprises as a main component propylene glycol, and the solvent system, the buffer, and the pH are selected such as to be effective to suppress formation of at least one of an amide degradation product, a first carbinolamide degradation product, and a second carbinolamide degradation product when the liquid formulation is stored under storage conditions (e.g., storage at 50° C. over 15 days). In especially preferred methods, the buffer is an aqueous acetate buffer at a concentration of between 0.05 and 0.25M and the pH of the formulation is pH 3.

Various objects, features, aspects and advantages of the inventive subject matter will become more apparent from the following detailed description of preferred embodiments.

DETAILED DESCRIPTION

The present invention is generally directed towards to pharmaceutical compositions and methods of preparing liquid and lyophilized formulations containing therapeutically effective concentrations of bortezomib, where the formulation provides significantly improved stability for bortezomib, especially where the formulation is a liquid formulation. Where the formulation is lyophilized or concentrated above the concentration suitable for injection, contemplated compositions will be administered after reconstitution with one or more pharmaceutically acceptable diluents, optionally further containing pharmaceutically acceptable antioxidants, stabilizers, preservatives and/or co-solvents.

In certain aspects of the inventive subject matter, contemplated formulations will include bortezomib and a hetero-bifunctional Lewis base donor to so form a donor acceptor complex, while in other aspects contemplated formulations are liquid formulations and will include an at least binary non-aqueous solvent system. In still further contemplated aspects, bortezomib and/or bortezomib donor acceptor complexes may also be encapsulated in a pharmaceutically acceptable delivery or carrier system, particularly in liposomes, micelles, nanoparticles, microspheres, emulsions, and/or suspensions. Regardless of the particular form of preparation, contemplated formulations may further include stabilizing agents, buffer components, anti-oxidants, isotonicity adjusting agents and lyoprotective agents.

Most typically, contemplated pharmaceutical formulations are stable for months at ambient conditions (i.e., 25° C., 60% relative humidity) when stored in an amber vial with nitrogen head space. Most typically, contemplated formulations will be subjected to sterile filtration, and when lyophilized, can be reconstituted with intravenous diluents such as saline, dextrose, or water for injection.

For example, in one preferred aspect, contemplated pharmaceutical compositions will include a liquid formulation that includes bortezomib in a substantially non-aqueous solvent system suitable for injection, and wherein the solvent system comprises propylene glycol as a main component. The term "substantially non-aqueous solvent system" refers to a solvent system in which bortezomib is completely soluble without water at a concentration of up to 10 mg/ml and that comprises water in a total amount of equal or less than 15 vol %. Where desired an antioxidant may be included in the formulation. As also used herein, the term "single phase" in conjunction with a solvent system refers to a composition in which multiple components do not separate into or exist in distinct phases. Therefore, liposomal formulations, emulsions, and suspensions are not considered single phase solvent systems. On the other hand, a mixture of two or more solvents that are miscible with each other are considered a single phase solvent system. In another preferred example, contemplated pharmaceutical compositions will include a formulation in which bortezomib and a hetero-bifunctional Lewis base form a Lewis donor-acceptor complex. Most typically, the hetero-bifunctional Lewis base has at least two distinct donor groups (preferably selected from the group of —$NH_2$, —SH, COOH, and —OH), and the formulation is lyophilized or in solution. As used herein, the term "donor acceptor complex" refers to a non-covalent and non-ionic association with a stability that is intermediate with respect to stability of covalent and ionic bonds.

Most preferably, bortezomib and the hetero-bifunctional Lewis base are present in a ratio of 1:100 to 1:200, more typically 1:10 to 1:100, and most typically 1:1 to 1:10. Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

In another preferred aspect, a storage-stable liquid pharmaceutical composition is contemplated that includes bortezomib in a therapeutically effective amount. As used herein, the term "storage-stable liquid pharmaceutical composition" refers to a liquid pharmaceutical composition in which the pharmaceutically active ingredient (bortezomib) is dissolved in a solvent or solvent system (which may comprise a buffer) at a ready-to-use concentration, and in which at least 99% of the pharmaceutically active ingredient remain in an undegraded state after storage of the composition over seven days at 50° C.

Most preferably, the composition comprises a single-phase liquid formulation comprising a substantially non-aqueous solvent system suitable for injection, a buffer, and bortezomib, wherein the bortezomib is present in the formulation at a therapeutically effective concentration. In most preferred aspects of the inventive subject matter, bortezomib will therefor be present at a concentration of between 0.1 mg/ml to 10.0 mg/ml, and more typically between 0.5 mg/ml and 5.0 mg/ml, and most typically between 1.0 mg/ml and 2.5 mg/ml, inclusive.

In particularly preferred aspects, the solvent system in such formulations has as a single and predominant component propylene glycol. Thus, the solvent system in especially preferred formulations essentially consists of propylene glycol. However, in less preferred aspects, the formulation may also include one or more additional solvents that are miscible with propylene glycol, and especially preferred co-solvents include polyethylene glycol and ethanol. Therefore, contemplated formulations will comprise at least 70 vol %, and more typically at least 90 vol % propylene glycol. As can be seen from the experimental data below, the chemical stability of bortezomib can be greatly increased by appropriate choice of the solvent system.

Likewise, while numerous pharmaceutically acceptable buffers are deemed appropriate for use herein, especially preferred buffers are aqueous buffers, and especially acetate buffer (see also results below). With respect to the strength of the buffer, it is generally preferred that the buffer is present in a concentration of between 0.01M and 0.5M, more typically between 0.025M and 0.3M, and most typically between 0.05M and 0.2M. The buffer will most preferably have a pH of 3.0, however, moderate modifications to that pH value are also contemplated. As is shown in more detail below, the inventors have discovered that contemplated bortezomib formulations have significantly and unexpectedly high stability at a pH that is about 3.0 in aqueous acetate buffer, particularly where the formulation has a substantially non-aqueous solvent system that has as a single and predominant component propylene glycol. Of course, it should be appreciated that similarly high stability may also be achieved with small deviations around pH 3.0. Determination of the preferred stability range around pH3 using acetate buffer can be performed without undue experimentation. Therefore, suitable pH values of the acetate buffer will typically also include pH ranges between 2.7 to 3.0 and 3.0 to 3.3.

Based on the experimental data below, the inventors therefore contemplate formulations that include bortezomib, a solvent system, and a buffer at a pH, wherein the solvent system and the pH are selected such as to be effective to suppress formation of an amide degradation product, a first carbinolamide degradation product, and/or a second carbinolamide degradation product when the liquid formulation is stored under storage conditions. As used herein, the term "suppress formation" with respect to degradation products (amide degradation product, first carbinolamide degradation product, and/or second carbinolamide degradation product) means that there is no detectable quantity (using a modified HPLC assay method as published in Journal of Pharmaceutical Sciences, 89, 2000, 758-765) of at least one of the degradation products in a formulation after storage over a period of at least seven days at a temperature of 50° C. Chromatographic conditions for the HPLC analysis of Bortezomib formulations used a Symmetry column, Waters C-8, 3.5μ, 4.6×150 mm at a column temperature of 30° C. Mobile phase was 68/32: water/acetonitrile containing 0.1% formic acid and 0.05% triethylamine at a flow rate of 1.0 mL/min and isocratic elution. UV Detection was performed at 270 nm, and injection volume was 10 μL.

It should be particularly noted that storage stability of liquid bortezomib composition is particularly important as bortezomib is highly instable in a wide variety of liquid solvents and conditions as is readily evident from published data and the experimental data below. As a consequence, most commercially available bortezomib compositions are therefore lyophilized compositions that need reconstitution with a solvent. However, once reconstituted, such solutions cannot be stored over extended periods without significant degradation, which precludes multi-dose liquid formulations for use in multiple patients and/or use for a single patient over a prolonged treatment period. Degradation of bortezomib in solution is a well-known phenomenon and an exemplary degradation scheme is depicted in Scheme I below. Here, compound II is a first carbinolamide degradation product, compound III is a second carbinolamide degradation product (which is a stereoisomer of II). Hydrolysis of II or III will lead to the formation of the corresponding amide IV, which can be further hydrolyzed to the carboxylic acid product V.

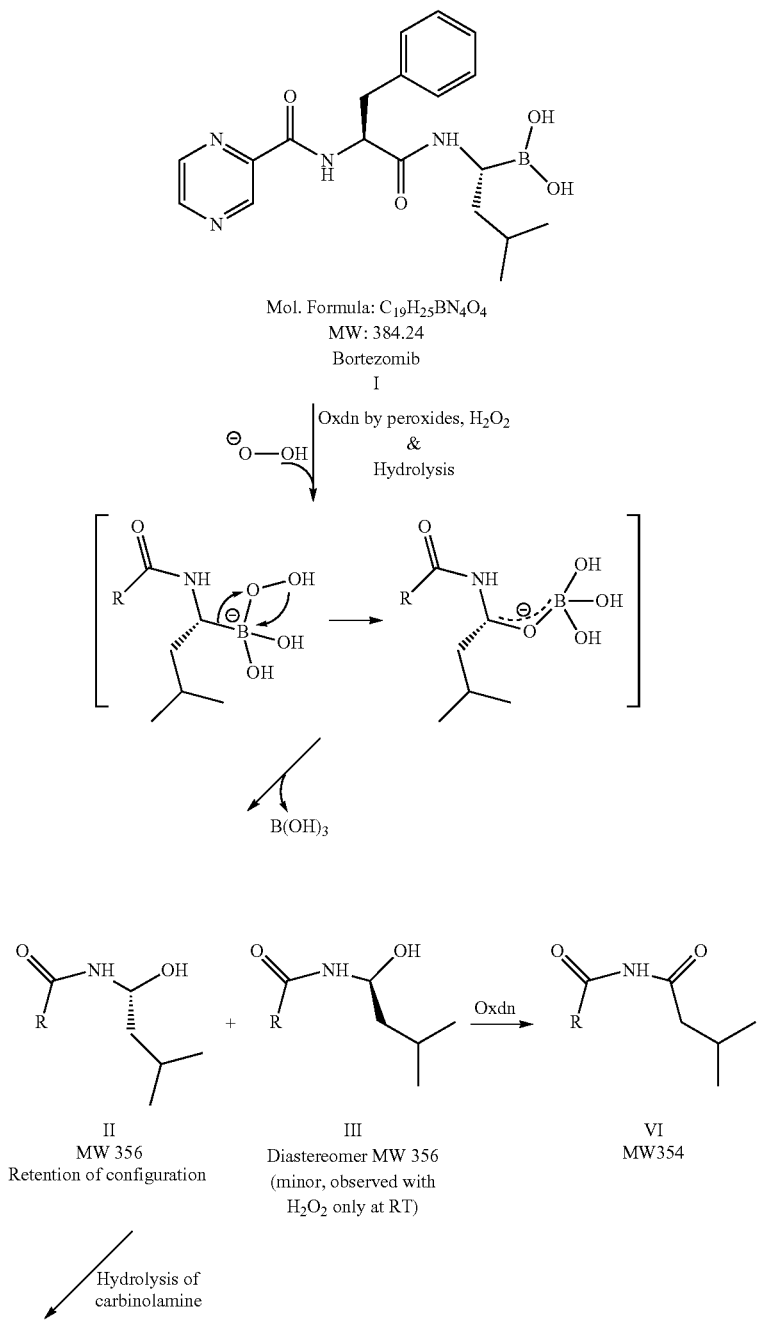

Therefore, and viewed from another perspective, the present inventive subject matter is drawn to compositions and pharmaceutical formulations comprising bortezomib in a stable liquid dosage form or as a stable lyophilized product. In most instances, the inventors contemplate that the pharmaceutical formulations in liquid forms provide stability of bortezomib at ambient conditions for at least two, more typically six, even more typically 12, and most typically 24 months and even longer. As further shown below (see examples, further data not shown), contemplated formulations provided significant stability to bortezomib in various solvent systems, and preferred solvent systems were formulated such that degradation of bortezomib was maintained at or below 10 wt %, more typically at or below 8 wt %, even more typically at or below 6 wt %, and most typically at or below 4 wt % and even at or below 2 wt % where the liquid formulation was stored over at least three months at ambient conditions.

With respect to storage stability, the inventors used model conditions well known in the art to predict or extrapolate storage stability under ambient conditions. For example, as can be seen from the experimental data below, the inventors used 'accelerated' storage conditions where formulations were stored at 40° C. and 75% relative humidity, and 'super accelerated' storage conditions where formulations were stored at 50° C. and 75% relative humidity for one month, which typically allows to predict or extrapolate corresponding stability data where the formulations is stored at ambient conditions for 16 months.

Similarly, where bortezomib is in lyophilized form, contemplated forms will provide stability of bortezomib at ambient conditions for at least two, more typically 6, and most typically 12 months and even longer. It should be appreciated that bortezomib may be present in contemplated pharmaceutical formulations in any suitable amount, and most preferably in an amount that is suitable for injection after reconstitution. Thus, and viewed from a different perspective, bortezomib is present in a therapeutically effective amount to treat a neoplastic (or other) condition in a human or other non-human mammal. In preferred aspects, bortezomib is present in a therapeutically effective amount to treat cancer. Typically, the bortezomib is present in an amount of about 0.01% to about 99% w/w of the total composition.

In especially preferred aspects, the non-aqueous solvent system is a single solvent or a binary solvent system, which may optionally further include a buffer. While various alternative solvents are also deemed suitable for use herein, particularly preferred solvents and solvent systems include propylene glycol, one or more short chain alcohols ($C_1$-$C_6$), dimethyl acetamide, N-methylpyrrolidone, dimethyl sulphoxide, and glycerol. Viewed from a different perspective, suitable solvents especially include polar non-protic and protic solvents. Where the solvent system is a binary system it is preferred that the solvents are two or more of short chain alcohols (e.g., ethanol, tert-butyl alcohol), aryl alcohols (e.g., benzyl alcohol), glycols (and especially propylene glycol), dimethyl acetamide N-methylpyrrolidone, and dimethyl sulphoxide.

Unexpectedly, the inventors further discovered that certain solvents allowed formation of a stable and liquid formulation, while closely related solvents lead to rapid degradation. For example, and as can be seen further below, propylene glycol allowed for formation of a stable solution of bortezomib while solutions with polyethylene glycol often lead to rapid degradation of the bortezomib. Similarly, ethanol in relatively low concentrations (e.g., equal or less than 25 vol %, more typically equal or less than 20 vol %) afforded a more stable formulation while ethanol quantities above 25 vol % led to marked degradation. It should further be appreciated that especially preferred solvents (e.g., propylene glycol, ethanol) will not lead to ester or di-ester formation, even in formulations with low (e.g., equal or less than 15 vol %) or no water content.

Likewise, it should be noted that bortezomib will not form an ester or di-ester with a (hetero-)bifunctional Lewis base donor molecule. Instead, bortezomib will form in most cases a donor acceptor complex that is intermediate in stability to an ionic bond and a covalent bond. Thus, the boronic acid moiety remains protected in solution or in lyophilized state without ester formation, leading to significantly improved stability. For example, suitable hetero-bifunctional Lewis base donors include compounds with two or more —OH, —SH, —COOH, and/or —$NH_2$ groups, which are most typically vicinal groups or separated by no more than 4 atoms in linear dimension. For example, suitable hetero-bifunctional Lewis base donors include compounds include compounds in which the two hetero-functional groups are —OH and —SH, —OH and —$NH_2$, —SH and —$NH_2$, —COOH and —$NH_2$, and —COOH and —SH.

A large variety of hetero-bifunctional Lewis base donors are known in the art and especially preferred donors include numerous amino acids (e.g., proteinogenic, essential, non-essential, chemically modified, synthetic, beta-, gamma-amino acids, etc. acids), all of which may be in D- or L-configuration. For example, contemplated amino acids include alanine, asparagine, aspartic acid, arginine, cysteine, glutamine, glycine, glutamic acid, histidine, isoleucine, lysine, leucine, phenylalanine, methionine, serine, proline, tryptophan, threonine, tyrosine and valine.

In further examples, the hetero-bifunctional Lewis base donor may also be a synthetic or natural peptide, and especially a dipeptide, a tripeptide, or an oligopeptide. Examples of peptides include carnosine, anserine, homoanserine, kyotorphin, balenine, aspartame, glorin, barettin, pseudoproline, glycylglycine, isoleucine-proline-proline (ipp), glutathione, thyrotropin-releasing hormone, melanostatin, ophthalmic acid, leupeptin, and eisenin. Oligopeptides are also deemed suitable, albeit less preferred.

In still further contemplated examples, hetero-bifunctional Lewis base donors may also be various polymers with pendant and/or terminal Lewis base donor groups. Among other preferred choices, especially suitable polymers include pharmaceutically acceptable polymers, including substituted polyethylene glycols with structure according to Formula I

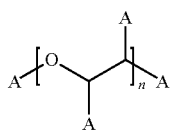

Formula I wherein n is an integer between 2 and 5,000, and wherein each A is independently selected from the group consisting of hydrogen, $-NH_2$, $-SH$, COOH, and $-OH$. In still further preferred aspects, the polymer may also comprise a carbohydrate backbone that is derivatized with two or more distinct Lewis donor groups. Of course, it should be appreciated that all polymers are especially that are pharmaceutically acceptable.

It should be further noted that the complex of the hetero-bifunctional Lewis base donor with bortezomib may be formed in numerous manners, and particularly suitable manners include heating in a solvent of choice for an appropriate period of time. Alternatively, complexes or esters can also be prepared by evaporation of solvent, salting out, or precipitation (facilitated by seeding). A further especially preferred manner is co-lyophilization of bortezomib with a hetero-bifunctional Lewis base donor, typically from an aqueous solution comprising of bortezomib and a molar excess of the hetero-bifunctional Lewis base donor. In some embodiments, the aqueous solution additionally comprises a (preferably water-miscible) co-solvent. Example of suitable co-solvents includes, but not limited to tert-butyl alcohol, methanol, ethanol, and mixtures thereof. While the molar excess of the hetero-bifunctional Lewis base donor relative to bortezomib can be in a wide range, it is generally preferred that the excess is between 1:1 to 1:200, more typically 1:100 to 1:200, even more typically 1:10 to 1:100, and most typically 1:1 to 1:10.

Depending on the particular formulation, contemplated compositions may comprise one or more bulking agent, cryoprotectant, or lyoprotectants to facilitate lyophilization. In some embodiments, the Lewis base donor molecule may also act as a bulking agent, cryoprotectant, lyoprotectants, and/or stabilizer. Further suitable lyoprotectants including amino acids, and polymers. Preferably, amino acids will be selected from lysine, alanine, glycine. Suitable polymers include various proteins (e.g., gelatin, albumin, etc.), polyethylene glycol, polyvinyl pyrrolidone, and Dextran-40. Most typically, the lyoprotectant represents less than 50% w/w of the total composition, and all concentrations above 1% w/w of the total composition are deemed effective to enhance the stability of the formulation. Thus, the lyoprotectant may be present in an amount of at least about 5% w/w, at least about 10% w/w, or at least about 20% w/w of the total composition.

The compositions contemplated herein may further include tonicity agents, and suitable tonicity agents include sodium chloride, glycerol, thioglycerol. Additionally, contemplated formulations may include further pharmaceutically acceptable excipients, and especially buffers, preservatives, and antioxidants, and any reasonable mixture thereof. However, in at least some formulations, the inventors unexpectedly discovered that formulations without antioxidants (and particularly without N-acetyl cysteine) had increased stability.

It should further be appreciated that depending on the particular ingredients, the pH of the formulation may vary. However, it is generally preferred that the pH of the formulations is suitable for injection and will typically be between 4.0 and 9.0, more typically between 5.5 and 8.0. Thus, one or more buffer systems may be employed to stabilize the pH at a desired value or range. Suitable buffers include citric acid buffer, acetic acid buffer, maleic acid buffer, phosphoric acid buffer, succinic acid buffer, and tartaric acid buffer. Most typically, the buffer strength is between 5 mM to 150 mM, however, higher and lower strengths are also deemed suitable for use herein. Remarkably, significant increases in stability were also observed where the solution was buffered with acetate buffer at pH 3 (or close to pH 3, typically between pH 2.7-3.3).

To still further improve the stability, the formulations may also include one or more anti-oxidants. For example, hydrophobic anti-oxidants include butylated hydroxytoluene, butylated hydroxyanisole, propyl gallate, and α-tocopherol, DL-tocopherol, α-tocopherol acetate, Tocopherol Polyethylene Glycol Succinate (Vitamin E TPGS), L-cysteine, or hydrophilic anti-oxidants, including sodium EDTA and thioglycerol. Most typically, the concentration of the anti-oxidant will be between 0.005% and 5% w/w of the total composition. Additionally, or alternatively, contemplated formulations may include a preservative (e.g., phenol, thimerosal, chlorobutanol, benzyl alcohol, m-cresol, phenoxyethanol, methylparaben and propylparaben), typically at a concentration of between 0.001% w/w and less than 5% w/w of the total composition, and most typically between 0.003% and 2.0% w/w of the total composition.

It should further be appreciated that contemplated formulations will be sterilized and all known manners of sterilization are deemed suitable for use herein, including filtration through 0.22 micron filters, heat sterilization, radiation (e.g., gamma, electron beam, microwave), and/or ethylene oxide sterilization to render the formulations sterile. Where contemplated formulations are lyophilized, they may be prepared as lyophilized cake, lyophilized powder, etc. The solutions or lyophilized forms may be diluted and/or reconstituted with standard intravenous diluents known in the art. For example, suitable intravenous diluents for use in the present invention include water, saline, dextrose 5% in water, water for injection or lactated ringer's solution.

Therefore, the inventors particularly contemplate a liquid pharmaceutical composition that includes bortezomib in a therapeutically effective amount, a substantially non-aqueous solvent system suitable for injection, and an aqueous buffer, wherein the composition has a pH that is equal or less than 4.0. In one especially preferred aspect, the liquid pharmaceutical composition comprises (a) bortezomib at a concentration of between 0.1 mg/ml to 10 mg/ml, more typically between 0.5 mg/ml to 5.0 mg/ml, and most typically between 1 mg/ml to 2.5 mg/ml, (b) propylene glycol as a predominant component (typically at least 50 vol %, more typically at least 70 vol %, even more typically at least 90 vol %, and most typically essentially consisting of propylene glycol) of the substantially non-aqueous solvent system, and (c) a non-chelating buffer or mono-dentate buffer, most preferably acetate buffer at a buffer strength of between 0.01 and 0.5M, and more typically between 0.05 and 0.25M, wherein the buffer has a pH of between 2.0 and 4.0, more typically between 2.3 and 3.7, and most typically between 2.7 and 3.3. Such compositions will exhibit equal or less than 10% degradation of bortezomib at accelerated storage conditions after 3 months, and more preferably equal or less than 7% degradation of bortezomib at accelerated storage conditions after 3 months, even more preferably equal or less than 5% degradation of bortezomib at accelerated storage conditions after 3 months, and most preferably equal or less than 3% degradation of bortezomib at accelerated storage conditions after 3 months. Thus, and viewed from a different perspective, contemplated compositions are storage-stable liquid pharmaceutical compositions.

For example, particularly preferred liquid pharmaceutical compositions comprise bortezomib at a concentration of between 1 mg/ml to 2.5 mg/ml, include propylene glycol in an amount of at least 70 vol % of the substantially non-aqueous solvent system, and further include acetate buffer at a buffer strength of between 0.05 and 0.25M, wherein the buffer has a pH between 2.7 and 3.3. Such compositions will exhibit equal or less than 10% degradation of bortezomib at accelerated storage conditions after 3 months.

In another example, particularly preferred liquid pharmaceutical compositions comprise bortezomib at a concentration of between 0.5 mg/ml to 5.0 mg/ml, include propylene glycol in an amount of at least 90 vol % of the substantially non-aqueous solvent system, and further include acetate buffer at a buffer strength of between 0.05 and 0.25M, wherein the buffer has a pH between 2.7 and 3.3. Such compositions will exhibit equal or less than 10% degradation of bortezomib at accelerated storage conditions after 3 months. In yet another example, particularly preferred liquid pharmaceutical compositions comprise bortezomib at a concentration of between 1 mg/ml to 2.5 mg/ml, include propylene glycol in an amount of at least 70 vol % of the substantially non-aqueous solvent system, and further include a non-chelating buffer (e.g., monocarboxylic acid buffer) or monodentate (i.e., only one complex bond is formed between one chemical group of the buffer molecule and the boron moiety of bortezomib) buffer at a buffer strength of between 0.05 and 0.25M, wherein the buffer has a pH between 2.3 and 3.7. Such compositions will exhibit equal or less than 10% degradation of bortezomib at accelerated storage conditions after 3 months.

In still another example, particularly preferred liquid pharmaceutical compositions comprise bortezomib at a concentration of between 1 mg/ml to 2.5 mg/ml, include propylene glycol in an amount of at least 90 vol % of the substantially non-aqueous solvent system, and further include acetate buffer at a buffer strength of between 0.05 and 0.25M, wherein the buffer has a pH between 2.3 and 3.7. Such compositions will exhibit equal or less than 10% degradation of bortezomib at accelerated storage conditions after 3 months.

In yet a further example, particularly preferred liquid pharmaceutical compositions comprise bortezomib at a concentration of between 1 mg/ml to 2.5 mg/ml, include propylene glycol in an amount of at least 70 vol % of the substantially non-aqueous solvent system, and further include acetate buffer at a buffer strength of between 0.05 and 0.25M, wherein the buffer has a pH between 2.7 and 3.3 (and most typically 3.0). Such compositions will exhibit equal or less than 10% degradation of bortezomib at accelerated storage conditions after 3 months.

Regardless of the particular formulation, it is especially preferred that the formulation is packaged in a container suitable for both single and multi use. Thus, especially preferred containers include an ampoule, a vial, a pre-filled syringe, and intravenous bag. Especially preferred multi-use containers will contain bortezomib in an amount suitable to allow at least two distinct uses, more typically at least five, and most typically at least ten distinct uses (each of which may or may not require the same quantity of formulation administered to the patient). Thus, particularly preferred containers will be configured as a multi-use container (e.g., contain a volume of the composition that is suitable for multiple and independent administrations), and especially preferred multi-use containers include vials with a rubber stopper that can be pierced with a needle of a syringe.

Thus, it should be appreciated that contemplated formulations will typically allow storage of the bortezomib for at least 1 week after first use, more typically at least 2-4 weeks after first use, and most typically at least 1-3 months (and even longer) after first use without significant degradation (i.e., less than 10% degradation, more typically less than 5% degradation) of the bortezomib under ambient conditions. Bortezomib may therefore be formulated for administration to human and various animals, and especially mammals. For example, formulations may be in the form of a solution for injection (e.g., injectable multi dose sterile composition), in the form of a sterile powdered composition (e.g., lyophilized cake, powder, lyophilized powder), which may be administered after dilution or reconstitution.

Therefore, the inventors also contemplate a method of suppressing formation of a plurality of degradation products of bortezomib in solution in which a single-phase liquid formulation is compounded from a substantially non-aqueous solvent system suitable for injection, a buffer, and bortezomib, wherein the bortezomib is present in the formulation at a pharmaceutically effective concentration. Most preferably, the solvent system comprises as a main component propylene glycol, and the solvent system, the buffer, and the pH are selected such as to be effective to suppress formation of an amide degradation product, a first carbinolamide degradation product, and a second carbinolamide degradation product when the liquid formulation is stored under storage conditions. With respect to the degradation products, the solvent system, the buffer, and the pH, the same considerations as noted above apply and are not reiterated here.

EXAMPLES

The following experiments are provided to exemplarily illustrate various aspects of the inventive subject matter presented herein. However, it should be apparent to those skilled in the art that many more modifications besides those already described are possible without departing from the inventive concepts herein.

Non-Aqueous Formulations (Set 1):

Five non-aqueous formulations were prepared with various ingredients shown in Table 1. More particularly, a stock solution of D/L-Tocopherol was made by dissolving 625 mg of D/L-Tocopherol in 25 ml of ethanol, and a stock solution of butylated hydroxytoluene (BHT) and butylated hydroxyanisole (BHA) were prepared by dissolving 15 mg of each in 100 ml of ethanol, respectively. All five formulations were prepared by dissolving, 20 mg of bortezomib in 200 proof 10 ml ethanol and 100 µl of DL Tocopherol ethanolic stock, 0.2 ml of BHT and BHA stock were added accordingly as per Table 1. Samples were then stored in an amber vial with nitrogen head space and stored at various storage conditions as indicated in the tables. The pH for the Formulations I-V was 4.0

TABLE 1

| Ingredients | Formulation I | Formulation II | Formulation III | Formulation IV | Formulation V |
|---|---|---|---|---|---|
| Bortezomib | 4.0 mg | 4.0 mg | 4.0 mg | 4.0 mg | 4.0 mg |
| Ethanol | 2.0 ml | 2.4 ml | 2.2 ml | 2.2 ml | 10.0 ml |
| Propylene Glycol | 8.0 ml | 7.6 ml | 7.8 ml | 7.8 ml | — |
| Dl Tocopherol % w/v | | 0.05 | 0.05 | 0.05 | |
| Butylated Hydroxy Toluene % w/v | | 0.00003 | | 0.00003 | |
| Butylated Hydroxy Anisole % w/v | | 0.00003 | | 0.00003 | |

Stability results are shown in Tables 2-4, wherein Table 2 lists results for the stability tests of bortezomib at 40° C. and 75% relative humidity, Table 3 lists results for the stability tests of bortezomib at 25° C. and 60% relative humidity, and Table 4 lists results for the stability tests of bortezomib at 4° C. Carbinolamide I is compound II of Scheme I; Carbinolamide II is compound III of Scheme I; Amide is compound IV of Scheme I; Carboxylic acid is compound V of Scheme I

TABLE 2

| | Formulation | | | | |
|---|---|---|---|---|---|
| | I | II | III | IV | V |
| Assay | | | | | |
| 1 Month | 93 | 91 | 94 | 91 | 76 |
| 2 Month | 95 | 91 | 93 | 94 | 65 |
| 3 Month | 93 | 91 | 92 | 92 | 51 |
| Amide | | | | | |
| 1 Month | 1.1 | 1.29 | 1.05 | 1.13 | 12 |
| 2 Month | 1.9 | 4.22 | 3.17 | 2.63 | 26 |
| 3 Month | 3.2 | 3.94 | 3.86 | 3.36 | 41 |
| Carboxylic acid | | | | | |
| 1 Month | 2.01 | 2.01 | — | 3.66 | 8.9 |
| 2 Month | 0.99 | 1.40 | 1.38 | 1.30 | 5.4 |
| 3 Month | 2.14 | 2.02 | 2.18 | 1.92 | 4.3 |
| Carbinolamide I | | | | | |
| 1 Month | 1.15 | 0.14 | 1.24 | 1.4 | 0.38 |
| 2 Month | 1.18 | 2.21 | 1.88 | 1.52 | 0.07 |
| 3 Month | 1.25 | 1.43 | 1.29 | 1.4 | 0.12 |
| Carbinolamide II | | | | | |
| 1 Month | — | — | — | 0.08 | — |
| 2 Month | 0.10 | 0.23 | 0.16 | 0.16 | 0.03 |
| 3 Month | 0.15 | 0.19 | 0.18 | 0.17 | 0.03 |
| Unknown (2.15 RRT) | | | | | |
| 1 Month | — | — | — | — | — |
| 2 Month | | 0.06 | 0.14 | | 0.12 | 1.79 |
| 3 Month | 0.17 | 0.19 | 0.19 | | 2.40 |

TABLE 3

| | Formulation | | | | |
|---|---|---|---|---|---|
| | I | II | III | IV | V |
| Assay | | | | | |
| 1 Month | 94.39 | 94.41 | 95.2 | 95.2 | 90.6 |
| 2 Month | 98.96 | 98.55 | 98.6 | 98.8 | 92.6 |
| 3 Month | 98.75 | 98.07 | 98.24 | 98.49 | 88.37 |

TABLE 3-continued

| | Formulation | | | | |
|---|---|---|---|---|---|
| | I | II | III | IV | V |
| Amide | | | | | |
| 1 Month | 0.1 | 0.13 | 0.08 | 0.11 | 1.38 |
| 2 Month | 0.2 | 0.27 | 0.26 | 0.23 | 2.91 |
| 3 Month | 0.27 | 0.38 | 0.35 | 0.33 | 5.44 |
| Carboxylic acid | | | | | |
| 1 Month | — | — | — | — | 4.55 |
| 2 Month | — | — | — | — | 3.62 |
| 3 Month | — | — | — | — | 5.15 |
| Carbinolamide I | | | | | |
| 1 Month | 0.73 | 0.91 | 0.8 | 0.94 | — |
| 2 Month | 0.62 | 1.03 | 0.9 | 0.72 | 0.06 |
| 3 Month | 0.77 | 1.04 | 1.21 | 1.04 | 0.07 |
| Carbinolamide II | | | | | |
| 1 Month | — | — | — | — | — |
| 2 Month | 0.06 | 0.08 | 0.07 | 0.07 | — |
| 3 Month | 0.07 | 0.09 | 0.09 | 0.08 | — |
| Unknown (2.15 RRT) | | | | | |
| 1 Month | — | — | — | — | — |
| 2 Month | — | — | — | — | 1.02 |
| 3 Month | — | — | — | — | 0.77 |

TABLE 4

| | Formulation | | | | |
|---|---|---|---|---|---|
| | I | II | III | IV | V |
| Assay | | | | | |
| 3 Month | 99.47 | 99.31 | 99.38 | 99.40 | 98.8 |
| Amide (0.72 RRT) | | | | | |
| 3 Month | 0.10 | 0.10 | 0.10 | 0.10 | 0.59 |
| Carboxylic acid | | | | | |
| 3 Month | — | — | — | — | — |
| Carbinolamide I | | | | | |
| 3 Month | 0.36 | 0.48 | 0.40 | 0.39 | 0.40 |
| Carbinolamide II | | | | | |
| 3 Month | 0.06 | 0.06 | 0.06 | 0.06 | 0.11 |
| Unknown (2.15 RRT) | | | | | |
| 3 Month | | | | | 0.07 |

Non-Aqueous Formulations (Set 2):

Five additional formulations were prepared with various ingredients as shown in Table 5. The formulations were prepared as follows: Degas the water for injection (WFI) to remove the dissolved oxygen in WFI and Propylene Glycol, refined Polyethylene Glycol 300 and Acetate buffer, weigh required amount of Bortezomib and add to the compounding vessel and dissolve in PG or PEG in the compounding vessel with stirring. After complete dissolution of the drug add remaining amount of vehicle such as propylene glycol, polyethylene glycol, and buffer. In case of the formulation with N-acetyl cysteine, add and dissolve N-acetyl cysteine in buffer under nitrogen and add to the drug solution. For formulations A-E the pH was 4.0

TABLE 5

| Ingredients | Concentration (mg/mL) | Batch Quantity |
|---|---|---|
| Formulation A | | |
| Bortezomib | 1 | 25.0 mg |
| Propylene Glycol | qs | 25 gm |
| Formulation B | | |
| Bortezomib | 1 | 25.0 mg |
| Refined PEG | qs | 25 gm |
| Formulation C | | |
| Bortezomib | 1 | 25.0 mg |
| Propylene Glycol | 45 | 22.5 gm |
| Acetate Buffer | 5 | 2.5 gm |
| Formulation D | | |
| Bortezomib | 1 | 25.0 mg |
| Propylene Glycol | 25 | 12.5 gm |
| Acetate Buffer | 25 | 12.5 gm |
| Formulation E | | |
| Bortezomib | 1 | 50.0 mg |
| Propylene Glycol | 25 | 25 gm |
| Acetate Buffer | 25 | 25 gm |
| N-Acetyl Cysteine | 5 | 0.250 gm |

Stability results are shown in Tables 6-8, wherein Table 6 lists results for the 2-week stability tests of bortezomib at indicated storage conditions, Table 7 lists results for the 6-week stability tests of bortezomib at indicated storage conditions, and Table 8 lists results for the 2-month stability tests of bortezomib at indicated storage conditions. ND=not detected using HPLC method as described above NA=not available; QL=Quantitation Limit; ND=Not Detected

TABLE 6

| Formulation | Initial | 2 Week | |
|---|---|---|---|
| Storage Condition | | 25° C./60% RH | 40° C./75% RH |
| Formulation A | | | |
| Bortezomib (1 mg/ml) in 100% PG | | | |
| Assay % | 100 | 100 | 99.5 |
| % Highest Impurity | ND | ND | 0.13 |
| Formulation D | | | |
| Bortezomib (1 mg/ml) in 50% PG and 50% Acetate Buffer | | | |
| Assay % | 99.65 | 99.86 | 99.26 |
| % Highest Impurity | ND | 0.14 | 0.62 |
| Formulation C | | | |
| Bortezomib (1 mg/ml) in 90% PG and 10% Acetate Buffer | | | |
| Assay % | 99.84 | 98.34 | 99.61 |
| % Highest Impurity | ND | 0.18 | ND |
| Formulation E | | | |
| Bortezomib (1 mg/ml) in 90% PG and 10% Acetate Buffer with NAC | | | |
| Assay % | 99.74 | 99.88 | 84.52 |
| % Highest Impurity | 0.16 | 0.12 | 7.11 |

TABLE 7

| Formulation | Initial | 6 Week | | |
|---|---|---|---|---|
| Storage Condition | | 0-4° C. | 25° C./60% RH | 40° C./75% RH |
| Formulation A | | | | |
| Bortezomib (1 mg/ml) in 100% PG | | | | |
| Assay % | 100 | 100 | 99.64 | 98.25 |
| % Highest Impurity | ND | ND | 0.14 | 0.65 |
| Formulation D | | | | |
| Bortezomib (1 mg/ml) in 50% PG and 50% Acetate Buffer | | | | |
| Assay % | 99.65 | 99.42 | 99.01 | 94.83 |
| % Highest Impurity | ND | 0.08 | 0.42 | 1.93 |
| Formulation C | | | | |
| Bortezomib (1 mg/ml) in 90% PG and 10% Acetate Buffer | | | | |
| Assay % | 99.84 | 99.85 | 99.56 | 98.34 |
| % Highest Impurity | | ND | 0.16 | 0.51 |
| Formulation E | | | | |
| Bortezomib (1 mg/ml) in 90% PG and 10% Acetate Buffer with NAC | | | | |
| Assay % | 99.74 | 62.36 | 91.64 | 44.21 |
| % Highest Impurity | 0.16 | 1.16 | 0.28 | 27.42 |

TABLE 8

| Formulation | Initial | 2 Month | | | 3 Month | | |
|---|---|---|---|---|---|---|---|
| | | 0-4° C. | 25° C./60% RH | 40° C./75% RH | 0-4° C. | 25° C./60% RH | 40° C./75% RH |
| Formulation A Bortezomib (1 mg/ml) in 100% PG | | | | | | | |
| Assay % | 100 | 99.79 | 99.32 | 97.46 | 99.73 | 99.77 | 96.11 |
| % Highest Impurity | ND | 0.07 | 0.23 | 0.98 | <QL | 0.11 | 1.7 |
| Formulation D Bortezomib (1 mg/ml) in 50% PG and 50% Acetate Buffer | | | | | | | |
| Assay % | 99.65 | 98.66 | 97.67 | 88.66 | 99.55 | 98.69 | 86.06 |
| % Highest Impurity | ND | 0.11 | 0.72 | 3.29 | 0.07 | 0.98 | 4.73 |
| Formulation C Bortezomib (1 mg/ml) in 90% PG and 10% Acetate Buffer | | | | | | | |
| Assay % | 99.84 | 99.68 | 99.41 | 96.28 | 99.68 | 99.58 | 94.65 |
| % Highest Impurity | | 0.07 | 0.15 | 1.06 | <QL | <QL | 1.74 |
| Formulation E Bortezomib (1 mg/ml) in 90% PG and 10% Acetate Buffer with NAC | | | | | | | |
| Assay % | 99.74 | 63 | 61 | 49.89 | | NA | NA |
| % Highest Impurity | 0.16 | 26 | 20.47 | 31.7 | | | |

Formulation B with PEG was not included in the study due to insolubility of the drug in PEG. As can be taken from the above results, stability of bortezomib is enhanced in the presence of PG. Formulation with 10% of aqueous buffer also showed a comparable stability to that of formulation with PG alone. However, an increase in the buffer concentration has revealed an undesirable increase in degradation products. Notably, the presence of a stabilizer/anti-oxidant like N-Acetyl Cysteine resulted in a significant degradation of the bortezomib.

Non-Aqueous Formulations (Set 3):

An additional six substantially non-aqueous formulations were prepared with various ingredients as shown in Table 9 and Table 10. The formulations were prepared as follows: Degas the buffer solutions and water for injection to remove the dissolved oxygen, weigh required amount of Bortezomib and add to the compounding vessel and dissolve in PG in the compounding vessel with stirring. After complete dissolution of the drug, add remaining amount of vehicle such as water for injection and buffer. Samples were then filled in amber vials with nitrogen head space and stored at 40° C./75% RH storage condition for duration of 3 months.

TABLE 9

| Ingredients | Formulation I | Formulation II | Formulation III | Formulation IV |
|---|---|---|---|---|
| Bortezomib | 10.0 mg | 10.0 mg | 10.0 mg | 10.0 mg |
| Propylene Glycol | 9.0 mL | 9.0 mL | 9.0 mL | 9.0 mL |
| Acetate Buffer (pH 4.0, 0.1M) | — | 1.0 mL | — | — |
| Acetate Buffer (pH 4.0, 0.5M) | — | — | 1.0 mL | — |
| Acetate Buffer (pH 4.0, 1M)) | — | — | — | 1.0 mL |
| W.F.I | 1.0 mL | — | — | — |

TABLE 10

| Ingredients | Formulation V | Formulation VI |
|---|---|---|
| Bortezomib | 10.0 mg | 10.0 mg |
| Acetate Buffer (pH 4.0, 0.1M) | 5.0 mL | 3.0 mL |
| Propylene Glycol | 5.0 mL | 7.0 mL |

Stability results are shown in Table 11, wherein Table 11 lists results for the stability tests of bortezomib stored at 40° C. and 75% relative humidity. The stability of these formulations were monitored to delineate the effect of buffer strength and the proportion of propylene glycol on the product stability. ND=not detected using HPLC method as described above; Carbinolamide I is compound II of Scheme I; Carbinolamide II is compound III of Scheme I; Amide is compound IV of Scheme I; Carboxylic acid is compound V of Scheme I.

TABLE 11

| Formulation | I | II | III | IV | V | VI |
|---|---|---|---|---|---|---|
| % Assay | | | | | | |
| 1 Month | 97.2 | 98.9 | 98.3 | 96.7 | 97.6 | 98.4 |
| 2 Month | 88.5 | 95.7 | 93.0 | 91.0 | 78.7 | 92.8 |
| 3 Month | 79.5 | 87.1 | 87.4 | 84.9 | 75.5 | 81.6 |
| Amide | | | | | | |
| 1 Month | 0.43 | 0.11 | 0.13 | 0.16 | 0.18 | 0.08 |
| 2 Month | 0.60 | 0.14 | 0.20 | 0.24 | 0.28 | 0.12 |
| 3 Month | 1.38 | 0.25 | 0.30 | 0.42 | 0.47 | 0.20 |
| Carboxylic Acid | | | | | | |
| 1 Month | 0.77 | 0.47 | 0.55 | 0.70 | 1.92 | 1.11 |
| 2 Month | 1.00 | 0.67 | 0.81 | 1.00 | 2.50 | 1.56 |
| 3 Month | 1.62 | 0.89 | 1.11 | 1.42 | 3.78 | 2.22 |
| Carbinolamide I | | | | | | |
| 1 Month | 1.16 | 0.33 | 0.5 | 0.56 | 0.15 | 0.24 |
| 2 Month | 1.38 | 0.46 | 0.56 | 0.75 | 0.15 | 0.29 |
| 3 Month | 2.39 | 0.61 | 0.79 | 1.01 | 0.16 | 0.35 |

TABLE 11-continued

| Formulation | I | II | III | IV | V | VI |
|---|---|---|---|---|---|---|
| Carbinolamide II | | | | | | |
| 1 Month | 0.36 | 0.11 | 0.13 | 0.19 | 0.05 | ND |
| 2 Month | 0.37 | 0.13 | 0.16 | 0.22 | 0.07 | 0.06 |
| 3 Month | 0.42 | 0.14 | 0.15 | 0.19 | 0.08 | 0.06 |

As can be taken from the above results, the stability of bortezomib seems to be compromised by increasing the buffer strength from 0.1M to 1 M. The order of stabilization with respect to the buffer strength being 0.1M>0.5M>1.0M. On a similar note, the formulations without any buffer showed decrease in the % assay and an increase in the related substances compared to the one with 0.1 M acetate buffer. In formulations V and VI, where the composition of aqueous phase was fixed and the proportion of PG was varied, the order of stabilization was 70% PG>50% PG.

Non-Aqueous Formulations (Set 4):

Several further compositions were prepared with various ingredients and various examples listed in Table 12. In this example, the possible effects of super-refined solvents on the stability of bortezomib was investigated essentially as described above. Solutions were prepared as follows: Degas the WFI to remove the dissolved oxygen in WFI and Propylene Glycol, Refined PG, refined Polyethylene Glycol 300 (PEG) and Acetate buffer, weigh required amount of Bortezomib and add to the compounding vessel and dissolve in PG and PEG in the compounding vessel with stirring to make 2 mg/ml solution. The stock solution was further diluted to 1 mg/ml by adding remaining amount of vehicle such as PG, PEG and acetate buffer. pH of all the formulations in Table 12 was 4.0

TABLE 12

Initial Potency of the Formulation With PEG and PG

| | Formulation with PG | | | Formulation with Super Refined PG | | | Formulation with Super Refined PEG | | |
|---|---|---|---|---|---|---|---|---|---|
| | 2 mg/ml | 1 mg/ml | 1 mg/ml with 20% acetate Buffer | 2 mg/ml | 1 mg/ml | 1 mg/ml with 20% acetate Buffer | 2 mg/ml | 1 mg/ml | 1 mg/ml with 20% acetate Buffer |
| % Assay | 99.2 | 99.2 | 99.2 | 99.12 | 99.1 | 99.37 | 95.8 | 94.8 | 95.8 |
| % Highest Impurity | 0.8 | 0.8 | 0.91 | 0.88 | ND | 0.63 | 4.2 | 5.17 | 4.19 |

Remarkably, the results indicate that there is no influence of the type of PG used in the formulation. However, the inventors have observed a significant degradation of bortezomib in the presence of super-refined PEG. This indicates that bortezomib can be stabilized in presence of propylene glycol, but apparently cannot be stabilized in the presence of a closely related alternative glycolic solvent, PEG under the experimental parameters as shown.

Non-Aqueous Formulations (Set 5):

Five substantially non-aqueous formulations were prepared with various ingredients as shown in Table 13. In these example formulations, the proportion of propylene glycol was fixed at 90%, the variable being the composition of the aqueous phase. In these formulations, citrate buffer, pH 4.0 and phosphate buffer pH, 7.4, each at two levels of ionic strength were used. Additionally, to measure the effect of ionic strength on the product stability, NaCl was added to increase the ionic strength to 0.5M. The formulations were prepared as follows: Degas the buffer solutions to remove the dissolved oxygen, weigh required amount of Bortezomib and add to the compounding vessel and dissolve in PG in the compounding vessel with stifling. After complete dissolution of the drug add remaining amount of vehicle such as propylene glycol and buffer. Samples were then filled in amber vials with nitrogen head space and stored at 'super accelerated' stability condition of 50° C. for duration of seven days.

TABLE 13

| Ingredients | Formulation VII | Formulation VIII | Formulation IX | Formulation X | Formulation XI |
|---|---|---|---|---|---|
| Bortezomib | 10.0 mg | 10.0 mg | 10.0 mg | 10.0 mg | 10.0 mg |
| Propylene Glycol | 9.0 mL | 9.0 mL | 9.0 mL | 9.0 mL | 9.0 mL |
| Citrate buffer (pH 4.0, 0.05M) | 1.0 mL | — | — | — | — |
| Citrate buffer (pH 4.0, 0.5M) | — | 1.0 mL | — | — | — |

TABLE 13-continued

| Ingredients | Formulation VII | Formulation VIII | Formulation IX | Formulation X | Formulation XI |
|---|---|---|---|---|---|
| Phosphate buffer (pH 7.4, 0.05M) | — | — | 1.0 mL | — | — |
| Phosphate buffer (pH 7.4, 0.5M) | — | — | — | 1.0 mL | — |
| Acetate Buffer (pH 4.0, 0.1M) | — | — | — | — | 1.0 mL |
| NaCl | — | — | — | — | 0.29 g |

Stability test results are shown in Table 14. Carbinolamide I is compound II of Scheme I; Carbinolamide II is compound III of Scheme I; Amide is compound IV of Scheme I; Carboxylic Acid is compound V of Scheme I.

TABLE 14

| | Formulation | | | | |
|---|---|---|---|---|---|
| | VII | VIII | IX | X* | XI* |
| % Assay | | | | | |
| 0 | 99.8 | 99.7 | 99.9 | — | — |
| 3 days | 99.5 | NT | 98.8 | — | — |
| 7 days | 94.7 | 95.9 | 95.3 | — | — |
| Amide | | | | | |
| 0 | ND | ND | ND | — | — |
| 3 days | 0.30 | NT | 0.18 | — | — |
| 7 days | 1.70 | 0.55 | 1.38 | — | — |
| Carboxylic Acid | | | | | |
| 0 | ND | ND | ND | — | — |
| 3 days | 0.20 | NT | 0.16 | — | — |
| 7 days | 0.51 | 0.97 | 0.49 | — | — |
| Carbinolamide I | | | | | |
| 0 | ND | ND | ND | — | — |
| 3 days | ND | NT | 0.06 | — | — |
| 7 days | 0.45 | 0.37 | 0.40 | — | — |
| Carbinolamide II | | | | | |
| 0 | ND | ND | ND | — | — |
| 3 days | ND | NT | 0.63 | — | — |
| 7 days | 1.33 | 0.40 | 1.22 | — | — |

Addition of Propylene Glycol to the respective aqueous phases of formulations X and XI led to the precipitation of the buffer salts. And hence, the stability analysis of these formulations was not feasible. Comparing the seven day accelerated stability results it was observed that the formulations with phosphate buffer, pH 7.4 were the least stable followed by the formulations with citrate buffer, pH 4.0 (moderate stability).

Non-aqueous Formulations (Set 6): To further delineate the effect of pH on the stability of bortezomib, seven substantially non-aqueous formulations (F-XII to F-XVIII) were prepared with various ingredients as shown in Table 15. In these example formulations the proportion of propylene glycol was fixed at 90%, while varying the pH of the aqueous phase from pH 2.2- to 5.0. The formulations were prepared as follows: Degas the buffer solutions to remove the dissolved oxygen, weigh required amount of Bortezomib and add to the compounding vessel and dissolve in PG in the compounding vessel with stirring. After complete dissolution of the drug add remaining amount of vehicle such as propylene glycol and buffer. Samples were then filled in amber vials with nitrogen head space and stored at 'super accelerated' stability condition of 50° C. for duration of 15 days.

TABLE 15

| Ingredients | F-XII | F-XIII | F-XIV | F-XV | F-XVI | F-XVII | F-XVIII |
|---|---|---|---|---|---|---|---|
| Bortezomib | 10.0 mg | 10.0 mg | 10.0 mg | 10.0 mg | 10.0 mg | 10.0 mg | 10.0 mg |
| Propylene Glycol | 9.0 mL | 9.0 mL | 9.0 mL | 9.0 mL | 9.0 mL | 9.0 mL | 9.0 mL |
| Acetate Buffer (pH 3.0, 0.1M) | — | 1.0 mL | — | — | — | — | — |
| Acetate Buffer (pH 5.0, 0.1M) | — | — | 1.0 mL | — | — | — | — |
| Acetate Buffer (pH 4.0, 0.1M) | — | — | — | 1.0 mL | — | — | — |
| Potassium Chloride/Hcl Buffer (pH 2.2, 0.1M) | — | — | — | — | 1.0 mL | — | — |
| Potassium Hydrogen phthalate/HCl buffer (pH 2.2, 0.1M) | — | — | — | — | — | 1.0 mL | — |
| Citrate Buffer (pH 3.0, 0.1M) | — | — | — | — | — | — | 1.0 mL |
| W.F.I, pH 4.0 | 1.0 mL | — | — | — | — | — | — |

Stability results are shown in Table 16. Carbinolamide I is compound II of Scheme I; Carbinolamide II is compound III of Scheme I; Amide is compound IV of Scheme I; Carboxylic Acid is compound V of Scheme I.

TABLE 16

| Formulation | XII | XIII | XIV | XV | XVI | XVII | XVIII |
|---|---|---|---|---|---|---|---|
| % Assay | | | | | | | |
| 0 | 101.2 | 100.9 | 100.5 | 101.2 | 100.1 | 99.2 | 100.2 |
| 3 days | 100.5 | 100.5 | 93.6 | 100.6 | 89.2 | 91.9 | 69.1 |
| 7 days | 94.4 | 100.5 | 85.9 | 95.3 | 79.7 | 86.5 | 58.2 |
| 15 days | NT | 99.8 | NT | NT | NT | NT | NT |
| Amide | | | | | | | |
| 0 | ND | ND | ND | ND | ND | ND | ND |
| 3 days | 0.08 | ND | 0.20 | ND | 0.95 | 0.59 | 1.74 |
| 7 days | 0.13 | ND | 0.79 | 0.06 | 1.96 | 1.25 | 2.65 |
| 15 days | — | ND | — | — | — | — | — |
| Carboxylic Acid | | | | | | | |
| 0 | ND | ND | ND | ND | ND | ND | ND |
| 3 days | 0.10 | 0.07 | 0.25 | 0.10 | 0.21 | 0.19 | 0.22 |
| 7 days | 0.26 | 0.12 | 0.23 | 0.23 | 0.35 | 0.32 | 0.33 |
| 15 days | — | 0.42 | — | — | — | — | — |
| Carbinolamide I | | | | | | | |
| 0 | ND | ND | ND | ND | ND | ND | ND |
| 3 days | ND | ND | 0.72 | ND | 0.05 | ND | 0.03 |
| 7 days | 0.30 | ND | 0.14 | 0.16 | 0.02 | ND | 0.04 |
| 15 days | — | ND | — | — | — | — | — |
| Carbinolamide II | | | | | | | |
| 0 | ND | ND | ND | ND | ND | ND | ND |
| 3 days | 0.08 | ND | 0.21 | 0.06 | 0.41 | 0.26 | 4.9 |
| 7 days | 0.18 | ND | 0.12 | 0.10 | 0.60 | 0.38 | 3.58 |
| 15 days | — | ND | — | — | — | — | — |

The results of the 15 day 'super-accelerated' stability studies indicate that in addition to the propylene glycol proportion, the pH of the aqueous phase has an effect on the stability of bortezomib. Specifically, for the formulations with aqueous phase pH 3.0, the % assay at the end of 15 days was at 99.8, the highest among all the formulations screened. In comparison, in the formulations with the aqueous phase pH of 5.0 and pH 2.2, Bortezomib exhibited rapid degradation.

Non-Aqueous Formulations (Set 7):

A substantially non-aqueous formulations were prepared with various ingredients as shown in Table 17. The formulations were prepared as follows: Degas the buffer solution and water for injection to remove the dissolved oxygen, weigh required amount of Bortezomib and add to the compounding vessel and dissolve in PG in the compounding vessel with stifling to make Bortezomib solution, followed by addition of appropriate amount of acetate buffer to make 2.5 mg/ml. The compositions were exerted 4° C. and ambient temperatures to monitor the physical stability. All the three compositions are physical stable, with Formulation XIX being the most preferred for administration of Bortezomib by subcutaneous route at a Bortezomib concentration of 2.5 mg/ml.

TABLE 17

| Ingredients | Formulation XIX | Formulation XX | Formulation XXI |
|---|---|---|---|
| Bortezomib | 25.0 mg | 25.0 mg | 25.0 mg |
| Propylene Glycol | 9.0 mL | 7.0 mL | 5.0 mL |
| Acetate Buffer (pH 3.0, 0.1M) | 1.0 mL | 3.0 mL | 5.0 mL |

Therefore, particularly preferred formulations will include those that are clear, colorless, sterile, self-preserved multi-dose, non-pyrogenic solution, preferably in two concentrations, 1 mg and 2.5 bortezomib per ml for intravenous (IV) and subcutaneous (SC) use respectively. Most preferably, such formulations will be provided in a 10-mL amber vial that contains 1 mg/mL of Bortezomib and a 5-mL vial that contains 2.5 mg/mL of bortezomib. Each vial of either size also contains 0.9 ml/1.0 ml of Propylene Glycol USP and 0.1 ml/mL of pH 3.0, 0.1 molar aqueous acetate buffer as exemplarily shown in Table 18.

TABLE 18

| | Composition 1 | Composition 2 |
|---|---|---|
| Bortezomib | 1 mg | 2.5 mg |
| Propylene Glycol USP | 0.9 mL | 0.9 mL |
| Aqueous Acetate Buffer, 0.1M, pH 3.0 | 0.1 mL | 0.1 mL |

Non-Aqueous Formulations (Set 8):

Substantially non-aqueous formulations were prepared with various ingredients as shown in Table 19. The formulations were prepared as follows: Degas the buffer solution and water for injection to remove the dissolved oxygen, weigh required amount of Bortezomib and add to the compounding vessel and dissolve in PG in the compounding vessel with stifling to make Bortezomib solution, followed by addition of appropriate amount of acetate buffer to make 1.0 mg/ml. The Bortezomib bulk solutions were filled into 10 mL amber type I vials with or without the nitrogen headspace. The compositions were then subjected to 2-8° C., ambient temperature (25° C./60% RH) and accelerated temperature (40° C./75% RH) to monitor the chemical stability, and results after 1 month storage are provided

TABLE 19

| Ingredients | Formulation XIX | Formulation XX | Formulation XXI |
|---|---|---|---|
| Bortezomib | 100.0 mg | 100.0 mg | 100.0 mg |
| Propylene Glycol | 50.0 mL | 70.0 mL | 90.0 mL |
| Acetate Buffer (pH 3.0, 0.1M) | 50.0 mL | 30.0 mL | 10.0 mL |

TABLE 20

| Storage | Headspace | Sample Name | % Assay | Amide | Carboxylic Acid | Carbinol-amide 1 | Carbinol-amide 2 |
|---|---|---|---|---|---|---|---|
| 2-8° C. | without $N_2$ | Formulation XIX | 98.7 | <QL | <QL | ND | 0.08 |
| | | Formulation XX | 99.0 | <QL | ND | ND | ND |
| | | Formulation XXI | 100.2 | <QL | ND | ND | <QL |
| | with $N_2$ | Formulation XIX | 99.6 | <QL | <QL | ND | <QL |
| | | Formulation XX | 99.9 | <QL | ND | ND | ND |
| | | Formulation XXI | 97.5 | <QL | ND | ND | 0.05 |
| 25° C./60% RH | without $N_2$ | Formulation XIX | 99.1 | 0.07 | 0.21 | ND | <QL |
| | | Formulation XX | 97.8 | <QL | 0.08 | ND | ND |
| | | Formulation XXI | 97.0 | <QL | <QL | ND | 0.05 |
| | with $N_2$ | Formulation XIX | 97.3 | 0.06 | 0.20 | ND | <QL |
| | | Formulation XX | 98.9 | <QL | 0.09 | ND | ND |
| | | Formulation XXI | 98.8 | <QL | <QL | ND | ND |
| 40° C./75% RH | without $N_2$ | Formulation XIX | 97.0 | 0.49 | 1.34 | <QL | <QL |
| | | Formulation XX | 97.3 | <QL | 0.54 | <QL | ND |
| | | Formulation XXI | 98.5 | <QL | 0.17 | <QL | <QL |
| | with $N_2$ | Formulation XIX | 97.6 | 0.32 | 1.16 | <QL | 0.18 |
| | | Formulation XX | 99.5 | <QL | 0.55 | <QL | ND |
| | | Formulation XXI | 100.2 | <QL | 0.18 | <QL | <QL |

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of manufacturing a ready to inject bortezomib-containing pharmaceutical article comprising:
   formulating a liquid parenteral formulation that contains bortezomib such that the formulation exhibits equal or less than 10% degradation of the bortezomib at accelerated conditions after 3 months;
   wherein the liquid parenteral formulation is prepared as a single-phase liquid formulation that comprises a substantially non-aqueous solvent system suitable for injection and including at least 50 vol % propylene glycol, an aqueous buffer, and bortezomib, wherein the bortezomib is present in the formulation at a therapeutically effective concentration; and
   packaging the liquid parenteral formulation in an amount sufficient for at least two distinct uses into a container, wherein the container is configured to allow providing multiple independent dosages of the liquid formulation.

2. The method of claim 1 wherein the liquid parenteral formulation is formulated such as to exhibit equal or less than 6% degradation of the bortezomib at ambient conditions after 3 months.

3. The method of claim 1 wherein the substantially non-aqueous solvent system includes at least 75 vol % propylene glycol.

4. The method of claim 1 wherein the liquid parenteral formulation has a pH that is equal or less than 4.0.

5. The method of claim 1 wherein the aqueous buffer has a buffer strength of between 0.05 and 0.25M.

6. The method of claim 1 wherein the bortezomib is present in the liquid parenteral formulation in an amount of between 0.5 mg/ml and 5.0 mg/ml.

7. The method of claim 1 wherein the amount is sufficient for at least ten distinct uses.

8. The method of claim 1 wherein the liquid parenteral formulation is formulated to allow storage at accelerated conditions over at least 1 month after first use without significant degradation of the bortezomib.

9. A bortezomib-containing pharmaceutical article, comprising:
   a liquid parenteral formulation contained in a container suitable for providing multiple independent dosages of the liquid formulation;
   wherein the liquid parenteral formulation is a single-phase liquid formulation and comprises a substantially non-aqueous solvent system suitable for injection that includes at least 50 vol % propylene glycol, an aqueous buffer, and bortezomib, wherein the bortezomib is present in the formulation at a therapeutically effective concentration;
   wherein the liquid parenteral formulation is present in an amount sufficient for at least two distinct uses; and
   wherein the liquid parenteral formulation is formulated such as to exhibit equal or less than 10% degradation of bortezomib at accelerated storage conditions after 3 months.

10. The pharmaceutical article of claim 9 wherein the container is a vial or a bag and contains the liquid formulation in an amount sufficient for at least five distinct uses.

11. The pharmaceutical article of claim 9 wherein the liquid parenteral formulation is sterile, and wherein the liquid formulation has not undergone lyophilization before accelerated storage for 3 months.

12. The pharmaceutical article of claim 9 wherein the substantially non-aqueous solvent system includes at least 75 vol % propylene glycol.

13. The pharmaceutical article of claim 12 wherein the liquid parenteral formulation has a pH that is equal or less than 4.0.

14. The pharmaceutical article of claim 13 wherein the aqueous buffer has a buffer strength of between 0.05 and 0.25M.

15. The pharmaceutical article of claim 13 wherein the aqueous buffer is an acetate buffer.

16. A method of using the bortezomib-containing parenteral formulation of claim 9, comprising:

withdrawing from a container a first dosage of a liquid bortezomib-containing pharmaceutical parenteral formulation for a first administration, wherein the container contains at least a second dosage of the liquid bortezomib-containing pharmaceutical parenteral formulation for a second administration;

storing the at least second dosage for at least one week;

withdrawing from the container the at least second dosage for the second administration.

17. The method of claim 16 further comprising a step of withdrawing from the container at least a third dosage.

18. The method of claim 16 wherein the step of storing comprises storage at 4° C. or ambient condition.

19. The method of claim 16 wherein the container is configured to include the liquid bortezomib-containing pharmaceutical formulation in an amount sufficient for at least ten distinct uses.

20. The method of claim 16 wherein the substantially non-aqueous solvent system includes at least 75 vol % propylene glycol, a buffer having a pH of equal or less than 4.0, and bortezomib at a concentration of between 0.5 mg/ml and 5.0 mg/ml.

* * * * *